United States Patent [19]

Malhotra

[11] 4,351,943
[45] Sep. 28, 1982

[54] PRODUCTION OF 6-(CHLORO OR SUBSTITUTED PHENOXY)-2-DI-(SUBSTITUTED PHENOXY)METHYL PYRIDINES

[75] Inventor: Sudarshan K. Malhotra, Walnut Creek, Calif.

[73] Assignee: The Dow Chemical Co., Midland, Mich.

[21] Appl. No.: 316,608

[22] Filed: Oct. 30, 1981

Related U.S. Application Data

[62] Division of Ser. No. 266,016, Sep. 18, 1980, Pat. No. 4,324,896.

[51] Int. Cl.$^3$ ............................................. C07D 213/51
[52] U.S. Cl. .................................. 546/301; 546/302; 546/270; 546/339
[58] Field of Search ................ 546/301, 302, 339, 270

[56] References Cited

U.S. PATENT DOCUMENTS 4,062,962  12/1977  Noveroske ..................... 424/263
4,163,787   8/1979  Malhotra et al. ................ 546/301

Primary Examiner—John M. Ford
Assistant Examiner—Bernard Dentz
Attorney, Agent, or Firm—Ronald G. Brookens; S. Preston Jones

[57] ABSTRACT

Compounds are prepared corresponding to the formula

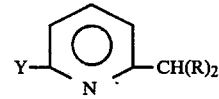

wherein Y represents chloro or R'; R represents

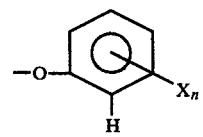

wherein X independently represents alkyl of 1 to 4 carbon atoms, alkoxy of 1 to 4 carbon atoms, alkylthio of 1 to 4 carbon atoms, alkyl sulfonyl of 1 to 4 carbon atoms, trifluoromethyl, chloro, fluoro or bromo; n represents an integer of 0 to 2 or $X_n$ represents 3,4-methylenedioxy and R' represents R with the proviso that R and R' can be the same or different. The compounds are useful as intermediates for the preparation of insecticidal substituted pyridine methyl esters of cyclopropane carboxylic acids.

19 Claims, No Drawings

PRODUCTION OF 6-(CHLORO OR SUBSTITUTED PHENOXY)-2-DI-(SUBSTITUTED PHENOXY)METHYL PYRIDINES

CROSS-REFERENCE TO RELATED APPLICATION

This is a divisional, of application Ser. No. 266,016, filed Sept. 18, 1980 now U.S. Pat. No. 4,324,896.

BACKGROUND OF THE INVENTION

Substituted phenoxy pyridine methyl esters of cyclopropane carboxylic acids are taught in U.S. Pat. No. 4,163,787 issued Aug. 7, 1979. These compounds are taught to be useful in the kill and control of various insect pest. These compounds are taught as being prepared by the reaction of an appropriate substituted phenoxy pyridine methanol with an appropriate 2,2-dimethyl-3-(2,2-dihaloethenyl)cyclopropane carboxylic acid halide.

While the above procedure is efficient in the preparation of the desired compounds, the cost of the substituted phenoxy pyridine methanols used in that procedure has made the so prepared desired compounds very expensive and less attractive for exploitation.

The substituted phenoxy pyridine methanols are prepared from the corresponding picolinaldehyde which in turn is made from the corresponding methyl picolinate. It is the cost of the above aldehyde and picolinate intermediates which makes the cost of the methanols so high. New processes for preparing these materials are being sought.

SUMMARY OF THE INVENTION

The present invention is directed to compounds corresponding to the formula

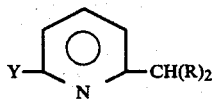

wherein Y represents chloro or R'; R represents

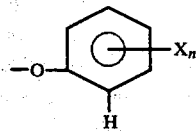

wherein X independently represents alkyl of 1 to 4 carbon atoms, alkoxy of 1 to 4 carbon atoms, alkylthio of 1 to 4 carbon atoms, alkyl sulfonyl of 1 to 4 carbon atoms, trifluoromethyl, chloro, fluoro or bromo; n represents an integer of 0 to 2 or $X_n$ represents 3,4-methylenedioxy and R' represents R with the proviso that R and R' can be the same or different; and to a method for making such compounds.

The present invention is also directed to the conversion of the above intermediate compounds to the corresponding picolinaldehydes, or in the use of those compounds wherein Y is chloro as intermediates to prepare additional intermediate compounds for conversion into the corresponding picolinaldehydes. The so prepared picolinaldehydes can in turn be converted to substituted phenoxy pyridine methanols. These latter compounds can then be reacted with an appropriate 2,2-dimethyl-3-(2,2-dihaloethenyl)-cyclopropane carboxylic acid halide, as taught in U.S. Pat. No. 4,163,787, to prepare insecticidal substituted pyridine methyl esters of cyclopropane carboxylic acids.

The 6-(chloro or substituted phenoxy)-2-di-(substituted phenoxy)methyl pyridines of the present invention are either solids or liquids which are only slightly soluble in water and usually are moderately to highly soluble in common organic solvents.

The compounds of the present invention can be prepared by the reaction of one mole of 2-chloro-6-(dichloromethyl)pyridine with from about 1 to about 3 moles of an alkali metal salt of at least one substituted phenol in the presence of a solvent.

Those compounds of the present invention wherein R and R' are the same can be prepared by the reaction of one mole of 2-chloro-6-(dichloromethyl)pyridine with 3 moles of an alkali metal salt of the appropriate substituted phenol in the presence of a solvent. This reaction scheme is as follows:

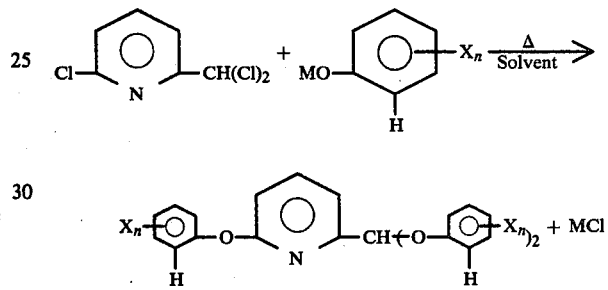

wherein X and n are as hereinbefore defined and M is sodium, potassium, lithium or cesium.

In carrying out this reaction, the pyridine reactant and the salt of the phenol are mixed together in the presence of a solvent and heated to a temperature of from about 100° to about 200° C. and stirred for from about 2 to about 24 hours. Thereafter, the reaction product is cooled, diluted with water and extracted with a solvent such as for example, 1,1,1-trichloroethane, methylene chloride, chloroform, ethyl acetate or ethyl ether. The solvent extract is water washed, dried and concentrated under reduced pressure and if desired, purified by distillation or other conventional methods.

The reaction consumes the reactants in stoichiometric proportions, i.e. one molar equivalent of the pyridine reactant to 3 molar equivalents of the phenol reactant. However, due to the nature of the reaction, it is preferred that a 5 to 25 percent excess of the phenol reactant be employed.

While the above procedure shows the use of an already prepared alkali metal salt of the phenol, this salt can be prepared in situ. In such a procedure, the pyridine reactant, an appropriate substituted methoxy phenol and an alkali metal hydroxide are mixed together with the solvent and then heated as set forth hereinabove. The alkali metal hydroxide is employed in a molar amount equal to that employed for the phenol reactant.

Representative solvents for use in carrying out this reaction include dimethyl sulfoxide, dimethyl formamide, N-methyl-2-pyrrolidone, toluene and xylene.

Those compounds of the present invention wherein Y is chloro can be prepared by the reaction of one mole of 2-chloro-6-(dichloromethyl)pyridine with 2 moles of an alkali metal salt of the appropriate substituted phenol in the presence of a solvent. This reaction scheme is as follows:

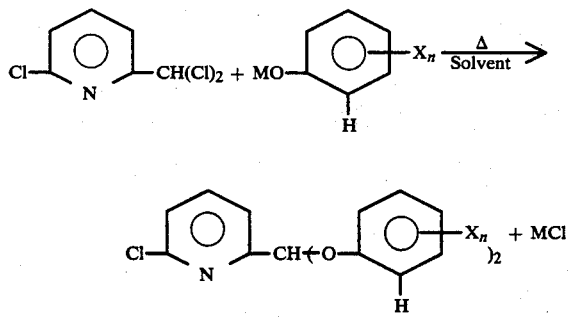

wherein X, n and M are as hereinbefore defined.

The reaction and the separation of the desired product can be carried out as set forth above for those compounds wherein R and R' are the same.

Those compounds of the present invention wherein R and R' are different can be prepared by the reaction of one mole of a 2-chloro-6-((disubstituted phenoxy)methyl)pyridine, prepared as above, with one mole of an alkali metal salt of the appropriate substituted phenol in the presence of a solvent. This reaction scheme is as follows:

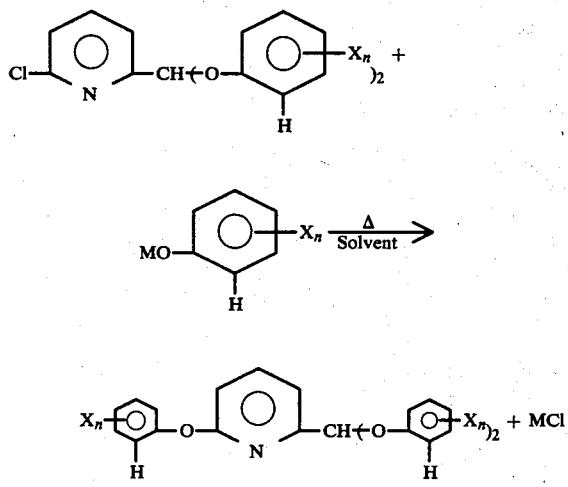

wherein X, n and M are as hereinbefore defined.

The reaction and the separation of the desired product can be carried out as set forth above for those compounds wherein R and R' are the same or wherein R' is chloro.

The 6-(substituted phenoxy)-2-di-(substituted phenoxy)methyl pyridine product can be hydrolyzed to the corresponding 6-(substituted phenoxy)picolinaldehyde by acid hydrolysis with an inorganic or organic acid and, if desired, in the presence of a solvent.

In carrying out the hydrolysis step, one mole of the 6-(substituted phenoxy)-2-di-(substituted phenoxy)methyl pyridine is mixed with an excess of an inorganic or organic acid such as, for example, sulfuric acid, dilute hydrochloric acid or acetic acid. The reaction can be conducted, if desired, in the presence of a solvent or reaction medium such as, for example, 1,4-dioxane, monoglyme or water. The mixture is heated to a temperature of from about 60° to about 150° C. for from about 10 minutes to 12 hours or more. The reaction product is cooled, diluted with water and extracted with a solvent such as, for example ethyl ether, methylene chloride or chloroform. The desired product can be recovered from the solvent extract by conventional recovery techniques which include, for example, water washing, washing with diluted sodium hydroxide and a saturated salt solution, drying and solvent removal under reduced pressure.

DESCRIPTION OF SOME PREFERRED EMBODIMENTS

The following examples further illustrate the present invention.

EXAMPLE I

2-Chloro-6-(diphenoxymethyl)pyridine

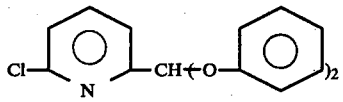

A mixture of 25 grams (g) (0.13 mole (m)) of 2-chloro-6-(dichloromethyl)pyridine, 29.91 g (0.32 m) of phenol and 17.84 g (0.32 m) of potassium hydroxide in 100 milliliters (ml) of dimethylsulfoxide was heated, with stirring, for 6 hours at 70° C. The reaction mixture was cooled, diluted with water and extracted with 1,1,1-trichloroethane. The extract was washed with water, dried over anhydrous magnesium sulfate and concentrated under reduced pressure. The concentrate was subjected to Kugelrohr distillation and 27.3 g of a yellow viscous liquid was recovered. This liquid was determined to be the desired 2-chloro-6-(diphenoxymethyl)pyridine by its nuclear magnetic resonance spectra and its elemental analysis. The product boiled at 150° C. at 0.1 millimeter of mercury (mm) and had a refractive index of $n_D^{25} = 1.5991$. The elemental analysis showed the product to have carbon, hydrogen and nitrogen contents of 68.63, 4.40 and 4.49 percent, respectively, as compared with the theoretical contents of 69.34, 4.49 and 4.49 percent, respectively, as calculated for the above named compound.

By following the preparative procedure as outlined in the above example, the following compounds set forth below in TABLE I can be prepared.

TABLE 1

[Structure: 2-chloro-6-(substituted) pyridine with CH(O-phenyl-X$_n$)$_2$ group]

| $X_n$ | Calculated C | H | N | Found C | H | N | Physical Property* |
|---|---|---|---|---|---|---|---|
| 4-Cl | 56.77 | 3.15 | 3.68 | 56.44 | 3.14 | 3.72 | $n\frac{25}{D} = 1.6063$ |
| 2-Cl | | | | | | | |
| 3-Cl | | | | | | | |
| 2-Cl; 4-Br | | | | | | | |
| 2-Br | | | | | | | |
| 3-OCH$_3$ | 64.60 | 4.85 | 3.77 | 64.28 | 4.98 | 3.47 | $n\frac{25}{D} = 1.5920$ |
| 4-Br | 46.01 | 2.56 | 2.98 | 45.31 | 2.63 | 2.85 | M.P. = 75°–78° C. |
| 2-CH$_3$ | | | | | | | |
| 4-CH$_3$ | 70.69 | 5.30 | 4.12 | 69.95 | 5.35 | 4.07 | $n\frac{25}{D} = 1.5850$ |
| 4-C$_4$H$_9$ | | | | | | | |
| 2-Cl; 4-CF$_3$ | | | | | | | |
| 2-CF$_3$ | | | | | | | |
| 3-CF$_3$ | 53.63 | 2.68 | 3.13 | 53.41 | 2.73 | 3.17 | $n\frac{25}{D} = 1.5146$ |
| 3-F | 62.16 | 3.45 | 4.03 | 61.45 | 3.62 | 4.03 | $n\frac{25}{D} = 1.5720$ |
| 4-F | 62.16 | 3.45 | 4.03 | 61.98 | 3.54 | 4.07 | $n\frac{25}{D} = 1.5705$ |
| 4-SCH$_3$ | 59.48 | 4.46 | 3.47 | 59.11 | 4.26 | 3.85 | |
| 3,5-(SCH$_3$)$_2$ | | | | | | | |
| 2-OC$_4$H$_9$ | | | | | | | |
| 2,4-O—C$_4$H$_9$ | | | | | | | |
| 4-OCH$_3$ | 64.60 | 4.85 | 3.77 | 64.38 | 4.99 | 3.56 | $n\frac{25}{D} = 1.5910$ |
| 4-SC$_4$H$_9$ | | | | | | | |
| 4-SO$_2$CH$_3$ | | | | | | | |
| 4-SO$_2$C$_4$H$_9$ | | | | | | | |
| 3,4-O—CH$_2$—O | | | | | | | |
| 3,5-(CF$_3$)$_2$ | | | | | | | |

*M.P. = Melting Point; $n\frac{25}{D}$ = Refractive Index

By following the preparative procedures as outlined above using ~one mole of the appropriate phenol or substituted phenol and one mole of the appropriate 2-chloro-6-(substituted phenoxy)pyridine, the following compounds can be prepared.

[Structure: pyridine with R' substituent and CH(R)$_2$ group, where R and R' are substituted phenoxy groups]

| R ($X_n$) | R' ($X_n$) |
|---|---|
| 4-Cl | 2-Cl |
| 2-Cl | 2-Cl; 4-Br |
| 3-Cl | 4-C$_4$H$_9$ |
| 2-Cl; 4-Br | 2-Cl; 4-CF$_3$ |
| 2-Br | 2-Cl |

-continued

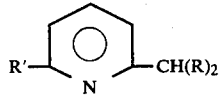

| R | R' |
|---|---|
| 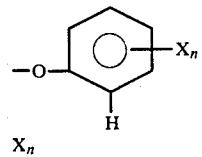 | 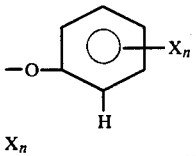 |
| $X_n$ | $X_n$ |
| 4-Br | 3-Cl |
| 2-CH$_3$ | 4-C$_4$H$_9$ |
| 4-CH$_3$ | 2-CH$_3$ |
| 4-C$_4$H$_9$ | 2-F |
| 2-Cl; 4-CF$_3$ | 2-Cl |
| 2-CF$_3$ | 2-Cl |
| 3-CF$_3$ | 2-CF$_3$ |
| 3-F | 4-F |
| 4-F | 3-F |
| 4-SCH$_3$ | 2-Cl |
| 3,5-(SCH$_3$)$_2$ | 4-SCH$_3$ |
| 2-OC$_4$H$_9$ | 2-OCH$_3$ |
| 2,4-OC$_4$H$_9$ | 2-OCH$_3$ |
| 2-OCH$_3$ | 4-OCH$_3$ |
| 3-OCH$_3$ | 4-SCH$_3$ |
| 4-SC$_4$H$_9$ | 2-Cl |
| 4-SO$_2$CH$_3$ | 2-Cl |
| 4-SO$_2$C$_4$H$_9$ | 2-OC$_4$H$_9$ |
| 3,4-O—CH$_2$—O | 2-Cl |
| 3,5-(CF$_3$)$_2$ | 2-CF$_3$ |

EXAMPLE II

2-[Bis-(4-methoxyphenoxy)methyl]-6-(4-methoxyphenoxy)pyridine

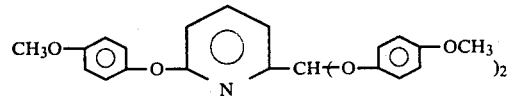

A mixture of 15.04 grams (g) (0.076 mole (m)) of 2-dichloromethyl-6-chloropyridine, 39.50 g (0.32 m) of p-methoxyphenol and 18.14 g (0.32 m) of potassium hydroxide in 100 milliliters (ml) of dimethylsulfoxide was heated, with stirring, for 72 hours. The resulting mixture was cooled to 25° C., diluted with water and extracted with 1,1,1-trichloroethane. The extract was washed with water, dried over anhydrous magnesium sulfate and concentrated under reduced pressure. The concentrate was subjected to Kugelrohr distillation removing as impurities any material boiling up to 200° C. at 0.05-1 millimeter of mercury (mm). The 2-[bis-(4-methoxyphenoxy)methyl]-6-(4-methoxyphenoxy)pyridine product was removed as the residue of the distillation and was a brown thick oil. The product was obtained in a yield of 25.3 g and upon analysis, was found to have carbon, hydrogen and nitrogen contents of 70.80, 5.37 and 3.09 percent, respectively, as compared with the theoretical contents of 70.59, 5.45 and 3.05 percent, respectively, as calculated for the above named compound.

By following the preparative procedure as outlined in the above example, the following compounds set forth below in Table II can be prepared.

TABLE II

| | Analysis | | | | | | |
|---|---|---|---|---|---|---|---|
| | Calculated | | | Found | | | |
| $X_n$ | C | H | N | C | H | N | Physical Property* |
| — | 78.03 | 5.18 | 3.79 | 77.96 | 5.30 | 3.83 | M.P. = 85°–86.5° C. |
| 4-Cl | 60.95 | 3.39 | 2.96 | 60.41 | 3.44 | 2.91 | |
| 2-Cl | | | | | | | |
| 3-Cl | | | | | | | $n\frac{25}{D} = 1.6728$ |
| 2-Cl; 4-Br | | | | | | | |
| 2-Br | | | | | | | |
| 4-Br | 47.52 | 2.64 | 2.31 | 47.04 | 2.71 | 2.22 | M.P. = 114°–116° C. |
| 2-CH$_3$ | | | | | | | |
| 4-CH$_3$ | 78.83 | 6.08 | 3.41 | 78.17 | 6.11 | 3.30 | $n\frac{25}{D} = 1.5955$ |
| 4-C$_4$H$_9$ | | | | | | | |
| 2-Cl; 4-CF$_3$ | | | | | | | |
| 2-CF$_3$ | | | | | | | |
| 3-CF$_3$ | 56.54 | 2.79 | 2.44 | 56.22 | 2.81 | 2.39 | $n\frac{25}{D} = 1.5096$ |
| 3-F | 68.09 | 3.78 | 3.31 | 67.84 | 3.88 | 3.22 | $n\frac{25}{D} = 1.5717$ |
| 4-F | | | | | | | |
| 4-SCH$_3$ | | | | | | | |
| 3,5-(SCH$_3$)$_2$ | | | | | | | |

TABLE II-continued

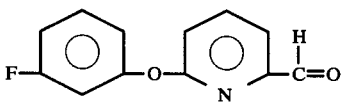

| $X_n$ | Analysis Calculated | | | Found | | | Physical Property* |
|---|---|---|---|---|---|---|---|
| | C | H | N | C | H | N | |
| 2-OC$_4$H$_9$ | | | | | | | |
| 2,4-OC$_4$H$_9$ | | | | | | | |
| 2-OCH$_3$ | | | | | | | |
| 4-SC$_4$H$_9$ | | | | | | | |
| 4-SO$_2$CH$_3$ | | | | | | | |
| 4-SO$_2$C$_4$H$_9$ | | | | | | | |
| 3,4-O—CH$_2$—O | 64.67 | 3.79 | 2.79 | 63.13 | 3.81 | 2.62 | |
| 3,5-(CF$_3$)$_2$ | | | | | | | |

*M.P. = Melting Point; $n\frac{25}{D}$ = Refractive index

EXAMPLE III 6-(3-Fluorophenoxy)picolinaldehyde

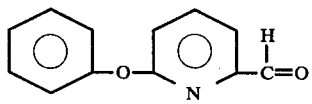

A solution of 2.5 g (0.0059 m) of 2-[bis-(3-fluorophenoxy)methyl]-6-(3-fluorophenoxy)pyridine and 20 ml of 80 percent acetic acid was heated, with stirring, at 150° C. overnight. The reaction mixture was cooled, diluted with water and extracted with methylene chloride. The extract was washed with water and concentrated under reduced pressure. The desired 6-(3-fluorophenoxy)picolinaldehyde which melted at 42°–43° C.

EXAMPLE IV 6-(phenoxy)-picolinaldehyde

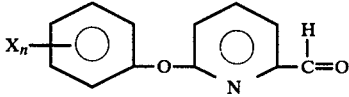

To a solution of 0.5 g of 2-[bis-(phenoxy)methyl]-6-(phenoxy)pyridine in 15 ml of 1,4-dioxane was added dropwise, 5 percent sulfuric acid until the mixture just became turbid. The mixture was heated over a steam bath at 80°–90° C. for about 10 minutes. The reaction mixture was poured into 20 ml of water, producing a yellowish emulsion and then extracted with 50 ml of ethyl ether. The extract was washed with 50 ml of a 5 percent aqueous sodium hydroxide solution and thrice with 50 ml portions of water and then with 50 ml of a saturated sodium chloride solution. The extract was then dried over sodium sulfate and the solvent removed by evaporation under reduced pressure. The residue was a yellow-orange oil which solidified partially on cooling to yield 0.3 g of the desired product. The product was confirmed by Infrared and Nuclear Magnetic resonance analysis.

By following the preparative procedures as outlined in the above Examples, the following compounds can be prepared.

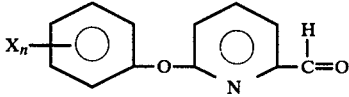

| $X_n$ |
|---|
| 2-Cl |
| 3-Cl |
| 4-Cl |
| 2-Cl; 4-Br |
| 2-Br |
| 4-Br |
| 3-F |
| 4-F |
| 2-CH$_3$ |
| 4-CH$_3$ |
| 4-C$_4$H$_9$ |
| 2-Cl; 4-CF$_3$ |
| 2-CF$_3$ |
| 3-CF$_3$ |
| 4-SCH$_3$ |
| 3,5-(SCH$_3$)$_2$ |
| 2-OC$_4$H$_9$ |
| 2,4-OC$_4$H$_9$ |
| 2-OCH$_3$ |
| 4-SC$_4$H$_9$ |
| 4-SO$_2$CH$_3$ |
| 4-SO$_2$C$_4$H$_9$ |
| 3,4-O—CH$_2$—O |
| 3,5-(CF$_3$)$_2$ |

Preparation of Starting Materials

The 2-(chloro-6-(dichloromethyl)pyridines employed as starting materials in the present invention are known compounds which can be prepared as taught in U.S. Pat. No. 3,687,827.

What is claimed is:

1. A process for the preparation of compounds corresponding to the formula

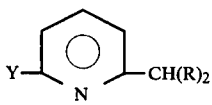

wherein Y represents chloro or R'; R represents

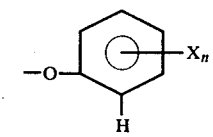

wherein X independently represents alkyl of 1 to 4 carbon atoms, alkoxy of 1 to 4 carbon atoms, alkylthio of 1 to 4 carbon atoms, alkyl sulfonyl of 1 to 4 carbon atoms, trifluoromethyl, chloro, fluoro or bromo; n represents an integer of 0 to 2 or $X_n$ represents 3,4-methylenedioxy and R' represents R with the proviso that R and R' can be the same or different, which comprises reacting one mole of 2-chloro-6-(dichloromethyl)pyridine with from about 1 to about 3 moles of an alkali metal salt of at least one substituted phenol which corresponds to the formula

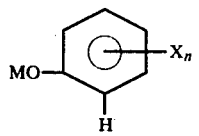

wherein M represents sodium, potassium, lithium or cesium at a temperature of from about 100° to about 200° C. and in the presence of a solvent and recovering the desired product therefrom.

2. The process as defined in claim 1 wherein Y is chloro.

3. The process as defined in claim 2 wherein one mole of 2-chloro-6-(dichloromethyl)pyridine is reacted with about one mole of the alkali metal salt of the substituted phenol.

4. The process as defined in claim 3 wherein a 5 to 25 percent excess of the phenol reactant is employed.

5. The process of claim 4 wherein the compound prepared is 2-chloro-6-(diphenoxymethyl)-pyridine.

6. The process of claim 4 wherein the compound prepared is 2-chloro-6-(bis(4-chlorophenoxy)-methyl)-pyridine.

7. The process of claim 4 wherein the compound prepared is 2-chloro-6-(bis(3-fluorophenoxy)-methyl)-pyridine.

8. The process of claim 4 wherein the compound prepared is 2-chloro-6-(bis(4-fluorophenoxy)-methyl)-pyridine.

9. The process as defined in claim 1 wherein Y is R' and R' represents R and R and R' are different.

10. The process as defined in claim 9 wherein 2-chloro-6-((disubstituted phenoxy)methyl)pyridine is first prepared and one mole of this material is reacted with about one mole of the alkali metal salt of the substituted phenol.

11. The process as defined in claim 1 wherein Y is R' and R' represents R and R and R' are the same.

12. The process as defined in claim 1 wherein one mole of 2-chloro-6-(dichloromethyl)pyridine is reacted with about 3 moles of the alkali metal salt of the substituted phenol.

13. The process as defined in claim 12 wherein a 5 to 25 percent excess of the phenol reactant is employed.

14. The process of claim 13 wherein the compound prepared is 2-[bis-(phenoxy)methyl]-6-(phenoxy)pyridine.

15. The process of claim 13 wherein the compound prepared is 2-[bis-4-methylphenoxy)methyl]-6-(4-methylphenoxy)pyridine.

16. The process of claim 13 wherein the compound prepared is 2-[bis-3-chlorophenoxy)methyl]-6-(3-chlorophenoxy)pyridine.

17. The process of claim 13 wherein the compound prepared is 2-[bis-4-chlorophenoxy)methyl]-6-(4-chlorophenoxy)pyridine.

18. The process of claim 13 wherein the compound prepared is 2-[bis-3-fluorophenoxy)methyl]-6-(3-fluorophenoxy)pyridine.

19. The process of claim 13 wherein the compound prepared is 2-[bis-4-fluorophenoxy)methyl]-6-(4-fluorophenoxy)pyridine.

* * * * *

UNITED STATES PATENT AND TRADEMARK OFFICE
CERTIFICATE OF CORRECTION

PATENT NO. : 4,351,943
DATED : September 28, 1982
INVENTOR(S) : Sudarshan K. Malhotra It is certified that error appears in the above—identified patent and that said Letters Patent is hereby corrected as shown below:

Column 3, line 62, "R and R' are" should read --R and Y are--.

Signed and Sealed this

Twenty-second Day of February 1983

[SEAL]

Attest:

GERALD J. MOSSINGHOFF

Attesting Officer

Commissioner of Patents and Trademarks